(12) United States Patent
Maass et al.

(10) Patent No.: US 9,545,524 B2
(45) Date of Patent: Jan. 17, 2017

(54) LIGHT THERAPY DEVICE

(75) Inventors: Henning Maass, Waalre (NL); Gary Garcia Molina, Eindhoven (NL); Henriette Van Vugt, Utrecht (NL); Adrienne Heinrich, Den Bosch (NL); Jia Du, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 798 days.

(21) Appl. No.: 13/991,720

(22) PCT Filed: Dec. 16, 2011

(86) PCT No.: PCT/IB2011/055752
§ 371 (c)(1),
(2), (4) Date: Jun. 5, 2013

(87) PCT Pub. No.: WO2012/085805
PCT Pub. Date: Jun. 28, 2012

(65) Prior Publication Data
US 2013/0268033 A1  Oct. 10, 2013

(30) Foreign Application Priority Data

Dec. 21, 2010  (EP) .................................. 10196215

(51) Int. Cl.
*A61N 5/06*  (2006.01)
(52) U.S. Cl.
CPC ........... *A61N 5/0613* (2013.01); *A61N 5/0618* (2013.01); *A61N 2005/0626* (2013.01); *A61N 2005/0642* (2013.01)
(58) Field of Classification Search
CPC ..... A61N 5/0613; A61N 5/0618; A61M 21/00
(Continued)

(56) References Cited

U.S. PATENT DOCUMENTS 6,652,512 B2   11/2003  Ota
6,718,128 B2    4/2004  Meyer et al.
(Continued)

FOREIGN PATENT DOCUMENTS

CN   1076791 A   9/1993
CN   1242712 A   1/2000
(Continued)

OTHER PUBLICATIONS

Shan et al: "Head Pose Estimation Using Spectral Regression Discriminant Analysis"; 2009 IEEE Computer Vision and Pattern Recognition Workshops, Jun. 2009, pp. 116-123.
(Continued)

*Primary Examiner* — Timothy J Neal

(57) ABSTRACT

A light therapy device (1) comprises: at least one light source (2); a control device (10) for controlling the operation of the light source; a boundary memory (11) containing boundary information defining boundaries for the distance (D) and relative angle (f) of a user's head with respect to the light source; monitoring means (30) for monitoring the actual distance and actual relative angle of the user's head and generating an output signal indicating the measured distance and angle. The control device has an input coupled to the memory for receiving the boundary information, and has an input coupled to the monitoring means for receiving the output signal from the monitoring means. The control device compares the output signal from the monitoring means with the boundary information, and issues a warning signal when the actual position and/or orientation of the user's head and/or eyes is/are outside said boundaries.

11 Claims, 1 Drawing Sheet

(58) Field of Classification Search
USPC ....... 607/88, 89, 96; 362/230; 606/3, 12, 13, 606/17; 392/412, 418
See application file for complete search history.

(56) References Cited

U.S. PATENT DOCUMENTS

| | | |
|---|---|---|
| 7,374,569 B2 | 5/2008 | Whatcott et al. |
| 2005/0073839 A1 | 4/2005 | Pederson et al. |

FOREIGN PATENT DOCUMENTS

| | | |
|---|---|---|
| CN | 1476812 A | 2/2004 |
| CN | 2643913 Y | 9/2004 |
| CN | 1618479 A | 5/2005 |
| CN | 2750819 Y | 1/2006 |
| CN | 1894577 A | 1/2007 |
| JP | 10153946 A | 6/1998 |
| JP | 2008107258 A | 5/2008 |
| WO | 9310857 A1 | 6/1993 |
| WO | 9747993 A1 | 12/1997 |
| WO | 2007104309 A2 | 9/2007 |
| WO | 2010007572 A1 | 1/2010 |
| WO | 2010076708 A1 | 7/2010 |
| WO | 2010076709 A1 | 7/2010 |
| WO | 2010142430 A1 | 12/2010 |

OTHER PUBLICATIONS

Morgenthaler et al: "Practice Parameters for the Clinical Evaluation and Treatment of Circadian Rhythm Sleep Disorders"; American Academy of Sleep Medicine1, vol. 30, No. 11, 2007, pp. 1445-1459.

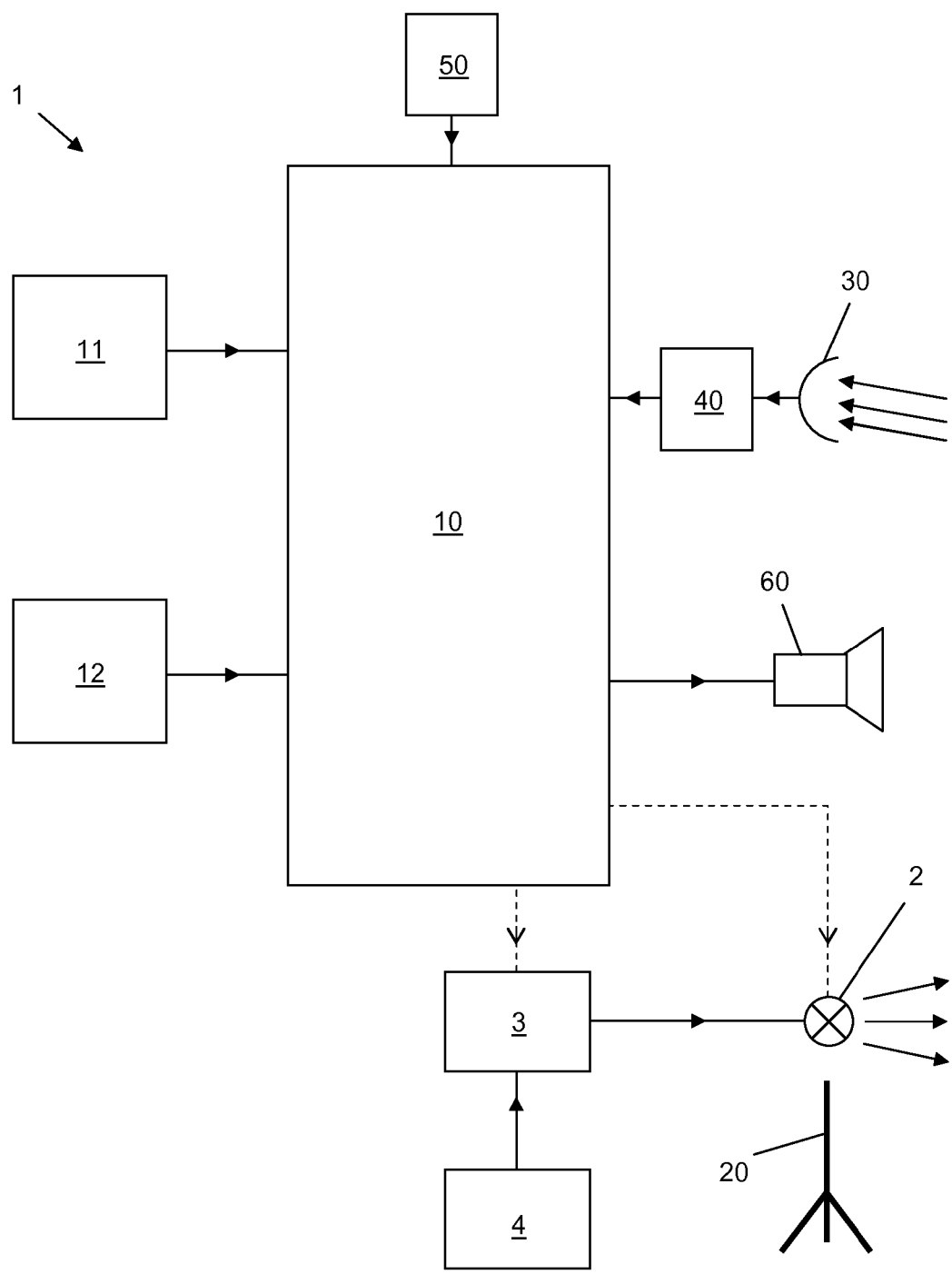

LIGHT THERAPY DEVICE

FIELD OF THE INVENTION

The present invention relates in general to a light therapy device. Although light can be used in a therapy for the skin, in the context of the present invention a light therapy device will be understood as being a device for generating light that can be and is intended to be perceived by the human eye.

BACKGROUND OF THE INVENTION

Light therapy of this type is for instance used for the treatment of affective disorders or circadian rhythm sleep disorders. Timed bright light therapy is the recommended treatment for Circadian Rhythm Sleep Disorders, especially for Shift Work Disorder and Delayed Sleep Phase Disorder; in this respect, reference can be made to the article "Practice Parameters for the Clinical Evaluation and Treatment of Circadian Rhythm Sleep Disorders" from the American Academy of Sleep Medicine in Sleep, Vol. 30, No. 11, 2007. Such therapy involves exposing patients at properly determined times to white light intensities of typically 2500-10,000 lux for periods ranging from 30 minutes to 2 hours. The most commonly used devices are small light boxes that have to be put on a table in front of the user. More recent light therapy devices make use of only the blue part of the light spectrum, because the shifting effect of the human circadian pacemaker system is most sensitive to blue light.

WO-2010/076708 discloses a device that comprises a head-mounted device in the shape of a mask: in such a case, the relative orientation and distance between the device and the user's eyes are always fixed.

SUMMARY OF THE INVENTION

In the case of 'free-standing' devices, which are placed on a floor, or on a desk, or which are mounted on a bedpost or the like, the relative orientation and distance between the device and the user's head or eyes may change when the user moves his head and/or his eyes. It is, however, important that the light therapy devices are operated within a pre-defined distance range to ensure that the light intensity that reaches the eyes is high enough to provide its therapeutic effect but low enough to avoid side effects such as eye strain, headache or even damage to the retina. For example, the prescribed operative distance range may be from 50-75 cm. Additionally, it is important that the user does not stare directly into the light source. Instead, the light therapy devices shall be positioned in such a way that the light reaches the eyes from above or below and from the side. In an ideal setup, the therapeutic light reaches the circadian system's photoreceptors inside the eye that are also present at the peripheral areas of the retina, but the therapeutic light does not reach the inner parts of the retina containing the photoreceptors for the vision functions of the eye.

Thus, for optimum effectiveness, comfort and safety, the correct position of the therapy device is important: the device (or more specifically its light source) should be positioned at a specific predefined distance from the user's head, and the light from the light source should enter the user's eyes at a predefined angle. Excessive proximity or small operating angles must be avoided as much as possible. On the other hand, if operated at large distances or large angles, the effectiveness of the therapy decreases because the amount of light that reaches the eye can become too low. This means that, taking a user's eye to define a coordinate system, the light source should be located at a well-defined fixed position with respect to this coordinate system. However, in the case of the 'free-standing' device, its position is stationary with respect to the fixed world, whereas the user may move his head. In practice, this means that the user must first correctly position the light therapy device relative to the user's eyes before starting the therapy session, and he/she must then ensure that for the duration of the session (e.g. between 30 and 60 minutes) the operating distance and angle are kept within the recommended limits. This aspect poses quite a challenge to the user. Especially if the user is engaged in other activities during the therapy session, it is likely that the user changes body and head position without noticing it. This can lead to situations that are dangerous to the safety or comfort of the user if the distance and/or angle become too small. On the other hand, if the distance and/or angle become too large, the desired therapeutic effect may not be achieved because the amount of light that reaches the circadian system's photoreceptors becomes too low.

WO-2007/104309 discloses a light therapy device with USB connection to a computer for the purpose of automatically switching on and off the device, based on presence information from a camera monitoring whether or not the user is sitting in front of the device. That invention aims to reduce unnecessary power consumption of the light therapy device while the user is not sitting in front of it.

WO-2010/007572 discloses a light therapy device that contains a distance sensor to control a shutter for limiting the region in which blue light is emitted by the device for the purpose of avoiding blue light hazard. The document does not disclose how a shutter mechanism could produce a light field in a way that specific areas of the human retina are exposed while other areas are not exposed. It seems that this document expects a user to be sitting in front of the device and looking straight into the lamp.

WO-1997/047993 discloses a wearable light therapy device in the form of goggles or eye-glasses that incorporates an eye-tracking sensor and an interactive light guide mesh to emit light only at the periphery of the pupil. The disadvantage of that device is that the user is forced to wear the therapy device on his/her head to solve the problem of maintaining the correct distance between the light source and the eyes.

It is an important objective of the present invention to provide a 'free-standing' light therapy device that can operate properly even if the user moves his head. It is a further important objective of the present invention to provide a light therapy device that can maintain safety and effectiveness even if the user moves his head.

To attain these objectives, the light therapy device according to the present invention comprises monitoring means, for instance a camera, monitoring the position and orientation of the user's head in general and his eyes in particular. Depending on the measured position and orientation of the user's head and/or eyes, the therapy device adapts its light output and/or generates a warning signal to the user.

Further advantageous elaborations are mentioned in the dependent claims.

BRIEF DESCRIPTION OF THE DRAWINGS

These and other aspects, features and advantages of the present invention will be further explained by the following description of one or more preferred embodiments with reference to the drawings, in which same reference numerals indicate same or similar parts, and in which:

FIG. 1 schematically shows a block diagram of a light therapy device.

DETAILED DESCRIPTION OF THE INVENTION

FIG. 1 schematically shows a block diagram of a light therapy device 1 according to the present invention, comprising a light source 2. The light source 2 may comprise one or more light-generating elements such as for instance fluorescent bulbs, LED arrays, etc, such as known per se, so that a more detailed description is not necessary here. In an example, the light source 2 is capable of generating a light intensity of 10,000 lux of white light or blueish white light. The light source 2 may, depending on type, be driven by a lamp driver 3 (known per se), and is powered from a power source 4, typically mains power. A control device 10 controls the operation of the light source 2 and/or its driver 3; the control device 10 may for instance be implemented as a microcontroller or microprocessor or the like, such as known per se, so that a more detailed description is omitted here.

This light therapy device 1 is designed for 'free-standing' use, and comprises fixing means 20 for placing the light source 2 with respect to the fixed world. In a simple embodiment, the fixing means 20 are implemented by just a lamp housing, to be placed on a table or desk, for instance. It is also possible that the fixing means 20 include a support of tripod design or the like.

The light therapy device 1 further comprises a monitoring device 30, typically and suitably, but not necessarily, implemented as a camera, capable of monitoring the position and orientation of the user's head and eyes (not shown for sake of simplicity). The monitoring device is mounted in close proximity to the light source 2, typically in or on the lamp housing. The light therapy device 1 further comprises a signal processing device 40, which may be a separate device or integrated with the monitoring device 30 or integrated with the control device 10. The signal processing device 40 may be implemented by image processing software in the case that the monitoring device 30 is implemented as a camera. The signal processing device 40 receives an output signal from the monitoring device 30, and processes this signal to determine the position and orientation of the user's head and/or eyes.

It is noted that methods of determining the position and attitude of a user's head, and of determining the orientation of the user's eyes, on the basis of camera images, are known per se. By way of example, reference is made to "Head Pose Estimation Using Spectral Regression Discriminant Analysis" by Caifeng Shan, Wei Chen in 2009 IEEE Computer Society Conference on Computer Vision and Pattern Recognition Workshops, Miami, Fla., USA, Jun. 20-Jun. 25, 2009, describing how a user's head pose can be estimated by processing video signals from a camera with an efficient subspace learning method: Spectral Regression Discriminant Analysis (SRDA). Therefore, a detailed explanation may be omitted here. Suffice it to say that the signal processing device 40 is capable of processing video signals from the monitoring device 30 in order to determine an angle $\phi$ between on the one hand a straight line between camera and eye and on the other hand the optical axis of the eye (determining the direction in which the user is looking). The angle $\phi$ thus determined or calculated is approximately equal to the angle at which the emitted bright light shines into the user's eyes.

Further, the signal processing device 40 is capable of processing video signals from the monitoring device 30 in order to estimate a distance D between the light therapy device and the user's face by measuring the diameter of the user's face as seen by the camera and converting the diameter into a corresponding distance using a manufacturer-calculated calibrated lookup table stored in a diameter conversion memory 13 associated with the control device 10. Since the device is for use by adult patients, it may be assumed that the sizes of the human head as observed by the camera do not differ too much from each other, so that the distance can be estimated from this value.

It is to be noted that the implementation of the present invention is not limited to this example.

The light therapy device 1 further comprises a boundary memory 11 associated with the control device 10. This boundary memory 11 contains information, for instance in the boundary of a look-up table, defining boundaries for the position and orientation of the user's head and/or eyes. Specifically, this boundary memory 11 contains values for a minimum distance Dmin, a maximum distance Dmax, a minimum angle $\phi$ min and a maximum angle $\phi$ max.

The light therapy device 1 further comprises a user-operable mode selector 50, for instance implemented as a set of keys, through which the user can select a treatment type. For instance, the user may select "awakening", or "jetlag", or "sleep disorder". The light therapy device 1 further comprises a second memory 12 associated with the control device 10. This second memory 12 contains information, for instance in the form of a look-up table, defining operative conditions for the different treatment types, such as for instance light colour and light intensity. It is also possible that different treatment types involve different boundary settings, for instance the angle of the light beam with respect to the user's eyes. It is possible that the second memory 12 is integrated with the boundary memory 11.

In operation, the control device 10 controls the settings of the light source 2 to achieve the light therapy selected by the mode selector 50, and receives the monitoring device's output signal(s), possibly processed by the processing device 40, reads the information from boundary memory 11, and compares the actual position and orientation of the user's head and/or eyes, as derived from the monitoring device's output signal(s), with the boundaries as defined by the information from boundary memory 11. As long as the control device 10 finds the actual position and/or orientation of the user's head and/or eyes to be within said boundaries, everything is well. As soon as the control device 10 finds that the actual position or orientation of the user's head and/or eyes is outside said boundaries, the control device 10 goes into warning mode. In this warning mode, the control device 10 activates a warning device 60 issuing a user-perceivable warning signal, indicating to the user that his head is not in the correct attitude. The warning signal may be a sound signal, in which case the warning device 60 may comprise a loudspeaker. The warning signal may also be a light signal, in which case the warning device 60 may comprise a separate light source, but it is also possible that the light source 2 is used for generating the warning signal. Alternatively or additionally, the control device 10 may change the settings of the light source 2 to adapt these settings to the measured position of the user's head. For instance, the control device 10 may decrease or increase the light output depending on the distance between the light source and the user's head.

In a first example, the device is capable of operating in a constant intensity mode, selectable by the mode selector 50.

In this mode, the light intensity of the light emitted by the light source 2 is constant, also selected by the user. In this mode, a minimum distance Dmin and a minimum angle φ min apply, of which the actual values depend on the user-selected light intensity. These actual values of Dmin and φ min may be stored in a look-up table, or may be calculated by the control device 10 on the basis of the values stored in memory 11, using a formula also stored in the memory 11. The control device 10 continuously or regularly compares the actual distance D with said minimum distance Dmin and compares the actual angle φ with said minimum angle φ min. The actual distance D should be larger than said minimum distance Dmin, and the actual angle φ should be larger than said minimum angle φ min. If the control device 10 finds that this condition is not met, the control device 10 goes into warning mode, issuing a safety warning to the user.

If said condition is not met, this poses a potential safety hazard. Therefore, in a more advanced embodiment, the control device 10 starts a timer as soon as it finds that said condition is not met. As soon as the timer value reaches a predefined threshold Tmax, indicating that the said condition has been violated for at least a time interval longer than Tmax, the control device 10 will enter a safety mode in which it reduces the light intensity to zero.

In a second example, the light intensity of the light emitted by the light source 2 is constant again, selected by the user, and the control device 10 is performing effectiveness monitoring, for which a maximum distance Dmax and a maximum angle φ max apply, of which the actual values depend on the user-selected light intensity. These actual values of Dmax and φ max may be stored in a look-up table, or may be calculated by the control device 10 on the basis of the values stored in memory 11, using a formula also stored in the memory 11. The control device 10 continuously or regularly compares the actual distance D with said maximum distance Dmax and compares the actual angle φ with said maximum angle φ max. The actual distance D should be smaller than said maximum distance Dmax, and the actual angle φ should be smaller than said maximum angle φ max. If the control device 10 finds that this condition is not met, the control device 10 goes into warning mode, issuing an effectiveness warning to the user.

A therapy session typically has a predefined (or user-selectable) duration. If said condition is not met, the effectiveness of the therapy session may be reduced. Therefore, in a more advanced embodiment, the control device 10 automatically increases the session duration by the sum of all time intervals during which said condition is violated. This makes sure that the minimally required exposure time to bright light with high-enough intensity is delivered to the user's eyes to ensure the desired therapeutic effect of the device.

In a third example, the control device 10 is operating in an automatic mode, as selected by the user via mode selector 50, in which the control device 10 measures the actual distance D and the actual angle φ and sets the light intensity of the light emitted by the light source 2 at an optimum value based on the measured values of D and φ. The intensity I is determined by the control device 10 by looking up the needed intensity value in a manufacturer-calculated calibrated lookup matrix stored in the memory. The rows and columns of the table are the measured values of D and φ and the pre-calculated required intensity I is stored in the cells of the matrix. The control device 10 fetches the cell value corresponding to the actual measurement parameters and controls the power of the lamp 2 accordingly. The intensity chosen is high enough to deliver the most effective therapeutic effect but low enough to ensure safety and comfort. For too small distances or angles, the device sets the intensity to zero and communicates a safety warning as described in the first example. For too large distances or angles, at which the light intensity of the device cannot be further increased to ensure the minimally required light dose, an effectiveness warning is communicated as described in the second example.

While the invention has been illustrated and described in detail in the drawings and foregoing description, it should be clear to a person skilled in the art that such illustration and description are to be considered illustrative or exemplary and not restrictive. The invention is not limited to the disclosed embodiments; rather, several variations and modifications are possible within the protective scope of the invention as defined in the appended claims.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope thereof.

In the above, the present invention has been explained with reference to block diagrams, which illustrate functional blocks of the device according to the present invention. It is to be understood that one or more of these functional blocks may be implemented in hardware, where the function of such functional block is performed by individual hardware components, but it is also possible that one or more of these functional blocks are implemented in software, so that the function of such one or more functional blocks is performed by one or more program lines of a computer program or a programmable device such as a microprocessor, microcontroller, digital signal processor, etc.

The invention claimed is:

1. Light therapy device comprising:
at least one light source;
a control device for controlling the operation of the light source;
a boundary memory containing boundary information defining boundaries for the distance (D) and relative angle (φ) of a user's head with respect to the light source, wherein the boundaries include a minimum distance (Dmin), a maximum distance (Dmax), a minimum angle (φ min) and a maximum angle (φ max);
monitoring means for monitoring the actual distance (D) and actual relative angle (φ) of the user's head with respect to the light source, and generating an output signal indicating the measured distance and angle;
wherein the control device has an input coupled to the boundary memory for receiving the boundary information;
wherein the control device has an input coupled to the monitoring means for receiving the output signal from the monitoring means;

wherein the control device is designed to compare the output signal from the monitoring means with the boundary information; and wherein the control device is designed to issue a warning signal when the comparison results indicate that the actual distance or actual angle of the user's head with respect to the light source is outside said boundaries.

2. Light therapy device according to claim 1, wherein said monitoring means comprise a camera mounted in close proximity to the light source.

3. Light therapy device according to claim 2, comprising a signal processing device capable of processing video signals from the monitoring device in order to determine an angle between on the one hand a straight line between camera and the user's eyes and on the other hand the optical axis of the user's eyes, wherein the angle thus determined is taken as approximation of said relative angle ($\phi$).

4. Light therapy device according to claim 2, comprising a signal processing device capable of processing video signals from the monitoring device in order to determine a distance (D) between the camera and the user's head by measuring the diameter of the user's head as seen by the camera and converting the diameter into a corresponding distance.

5. Light therapy device according to claim 1, further comprising a warning device capable of issuing a user-perceivable warning signal;

wherein the control device has an activation output coupled to the warning device; and wherein the control device is designed to issue the warning signal by activation of the warning device.

6. Light therapy device according to claim 1, further comprising a user-operable mode selector for allowing the user to select a predefined type of therapy.

7. Light therapy device according to claim 1, wherein the device is capable of operating in a constant intensity mode, in which the light intensity of the light emitted by the light source is constant;

wherein the minimum distance (Dmin) and the minimum angle ($\phi$ min) are determined depending on the user-selected light intensity;

wherein the control device is designed to compare the actual distance (D) with said minimum distance (Dmin) and to compare the actual angle ($\phi$) with said minimum angle ($\phi$ min); and wherein, if the control device finds that the actual distance (D) is smaller than said minimum distance (Dmin) or that the actual angle ($\phi$) is smaller than said minimum angle ($\phi$ min), the control device is designed to issue a safety warning to the user.

8. Light therapy device according to claim 7, wherein, if the control device finds that the actual distance (D) remains smaller than said minimum distance (Dmin) for more than a predetermined time interval (Tmax) or that the actual angle ($\phi$) remains smaller than said minimum angle ($\phi$ min) for more than a predetermined time interval (Tmax), the control device is designed to reduce the light intensity to zero.

9. Light therapy device according to claim 1, wherein the device is capable of operating in a constant intensity mode, in which the light intensity of the light emitted by the light source is constant;

wherein a therapy session duration is defined;

wherein the maximum distance (Dmax) and the maximum angle ($\phi$ max) are determined depending on the user-selected light intensity;

wherein the control device is designed to compare the actual distance (D) with said maximum distance (Dmax) and to compare the actual angle ($\phi$) with said maximum angle ($\phi$ max); and wherein, if the control device finds that the actual distance (D) is larger than said maximum distance (Dmax) or that the actual angle ($\phi$) is larger than said maximum angle ($\phi$ max), the control device is designed to issue an effectiveness warning to the user.

10. Light therapy device according to claim 9, wherein, if the control device finds that the actual distance (D) is larger than said maximum distance (Dmax) or that the actual angle ($\phi$) is larger than said maximum angle ($\phi$ max), the control device is designed to increase the therapy session duration by the sum of all time intervals during which either the actual distance (D) is larger than said maximum distance (Dmax) or the actual angle ($\phi$) is larger than said maximum angle ($\phi$ max), or both.

11. Light therapy device according to claim 1, wherein the device is capable of operating in an automatic mode, in which the control device measures the actual distance (D) and the actual angle ($\phi$) and sets the light intensity of the light emitted by the light source at an optimum value based on the measured values of distance and angle;

wherein the minimum distance (Dmin), the maximum distance (Dmax), the minimum angle ($\phi$ min) and the maximum angle ($\phi$ max) are determined;

wherein the control device is designed to compare the actual distance (D) with said minimum distance (Dmin) and with said maximum distance (Dmax) and to compare the actual angle ($\phi$) with said minimum angle ($\phi$ min) and with said maximum angle ($\phi$ max); and wherein, if the control device finds that the actual distance (D) is smaller than said minimum distance (Dmin) or that the actual angle ($\phi$) is smaller than said minimum angle ($\phi$ min), the control device is designed to set the light intensity to zero and/or to issue a safety warning to the user; and wherein, if the control device finds that the actual distance (D) is larger than said maximum distance (Dmax) or that the actual angle ($\phi$) is larger than said maximum angle ($\phi$ max), the control device is designed to issue an effectiveness warning to the user.

* * * * *